US 11,580,878 B2

(12) United States Patent
Redgård et al.

(10) Patent No.: US 11,580,878 B2
(45) Date of Patent: Feb. 14, 2023

(54) REAL TIME SPORTS MOTION TRAINING AID

(71) Applicant: West & Bergh Holding AB, Malamö (SE)

(72) Inventors: Fredrik Redgård, Lund (SE); Johan Nilsson, Staffanstorp (SE)

(73) Assignee: WEST & BERGH HOLDING AB, Malmo (SE)

( * ) Notice: Subject to any disclaimer, the term of this patent is extended or adjusted under 35 U.S.C. 154(b) by 127 days.

(21) Appl. No.: 16/638,965

(22) PCT Filed: Jun. 27, 2019

(86) PCT No.: PCT/EP2019/067208
§ 371 (c)(1),
(2) Date: Feb. 13, 2020

(87) PCT Pub. No.: WO2020/002527
PCT Pub. Date: Jan. 2, 2020

(65) Prior Publication Data
US 2020/0193865 A1    Jun. 18, 2020

(30) Foreign Application Priority Data

Jun. 28, 2018 (EP) .................... 18180484

(51) Int. Cl.
*G09B 19/00* (2006.01)
*A61B 5/11* (2006.01)
*G06V 40/20* (2022.01)

(52) U.S. Cl.
CPC ........ *G09B 19/0038* (2013.01); *A61B 5/1122* (2013.01); *G06V 40/23* (2022.01); *A61B 2503/10* (2013.01)

(58) Field of Classification Search
CPC . G09B 19/003; G09B 19/0038; A61B 5/1122; G06K 9/00342
See application file for complete search history.

(56) References Cited

U.S. PATENT DOCUMENTS 6,793,585 B1 * 9/2004 Miyamoto ......... A63B 24/0003
473/150
9,706,962 B1 * 7/2017 Uehara ................ A61B 5/0004
(Continued)

FOREIGN PATENT DOCUMENTS

CN       203763810 U    8/2014
CN       105530864 A    4/2016
(Continued)

OTHER PUBLICATIONS

Office Action for corresponding CN201980040645.9.
Office Action issued in connection with corresponding European Patent Application No. 18 180 484.0 dated Nov. 22, 2022.

*Primary Examiner* — Peter R Egloff
(74) *Attorney, Agent, or Firm* — Tarolli, Sundheim, Covell & Tummino LLP

(57) ABSTRACT

A sports training aid comprising a body unit, attachable to a person's body or the person's sports implement, is provided with a positioning sensor module; a feedback stimulator; and a processor. The sports training aid is configured to provide instantaneous feedback on motion faults of a studied sports motion, and the body unit is intended to be attached to a person's body (or a person's sports implement) at a representative location, the location being bound to travel a path representative of the studied sports motion, and the positioning sensor module comprises acceleration sensors and gyro sensors. The processor is configured to determine a still position corresponding to an event wherein the body unit is determined to be still, to keep track of the sensor module's movements relative to the still position, and to activate the (Continued)

feedback stimulator in real time, upon detection of a sports motion fault.

7 Claims, 17 Drawing Sheets

(56) References Cited

U.S. PATENT DOCUMENTS

| | | | |
|---|---|---|---|
| 10,213,645 B1* | 2/2019 | Wu | G06K 9/6277 |
| 2003/0109322 A1* | 6/2003 | Funk | A63B 69/3632 |
| | | | 473/219 |
| 2006/0084516 A1 | 4/2006 | Eyestone et al. | |
| 2007/0238538 A1* | 10/2007 | Priester | A63B 69/3608 |
| | | | 473/131 |
| 2012/0259578 A1 | 10/2012 | Bevilacqua et al. | |
| 2013/0128022 A1 | 5/2013 | Bose et al. | |
| 2014/0200094 A1* | 7/2014 | Parke | G06T 7/20 |
| | | | 473/409 |
| 2016/0199693 A1 | 7/2016 | Vermilyea et al. | |
| 2017/0021227 A1* | 1/2017 | Hayaishi | G06V 40/23 |
| 2017/0120124 A1 | 5/2017 | Hagiwara | |
| 2017/0274256 A1* | 9/2017 | Brekke | G01S 19/19 |

FOREIGN PATENT DOCUMENTS

| | | |
|---|---|---|
| CN | 106823345 A | 6/2017 |
| CN | 107871530 A | 4/2018 |
| EP | 3252736 A1 | 12/2017 |

\* cited by examiner

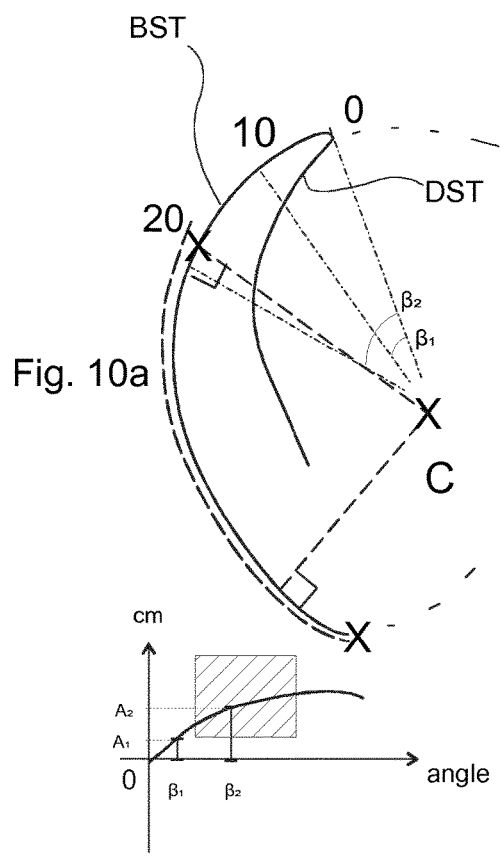
Fig. 10a
Fig. 10c
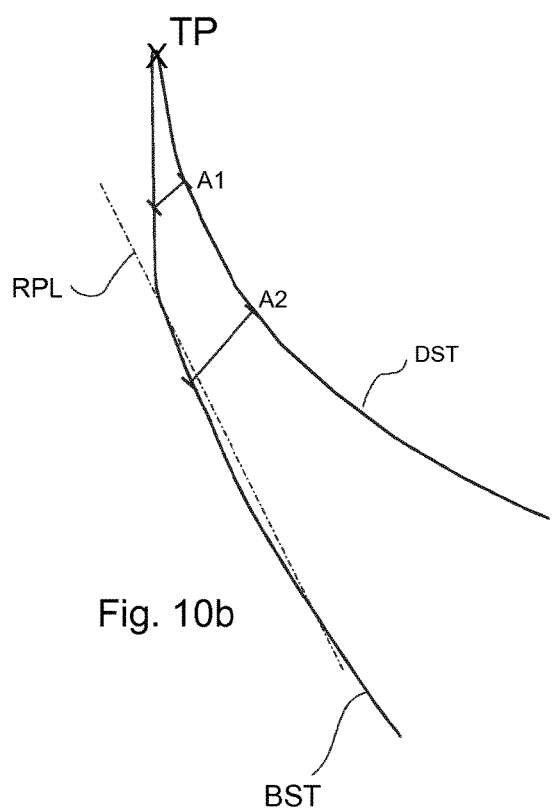
Fig. 10b

REAL TIME SPORTS MOTION TRAINING AID

RELATED APPLICATIONS

The present invention is a U.S. National Stage under 35 USC 371 patent application, claiming priority to Serial No. PCT/EP2019/067208, filed on 27 Jun. 2019; which claims priority of EP 18180484.0, filed on 28 Jun. 2018, the entirety of both of which are incorporated herein by reference.

TECHNICAL FIELD

The present invention relates to the field of training aids, i.e., devices that helps a person or animal better perform some activity of that person or animal. More particularly the present invention relates to a training aid providing feedback on a motion.

PRIOR ART

One example of such a motion training aid is known from WO2003024544. It discloses a repetitive motion feedback system provided with various sensors and devices for monitoring aspects of a repetitive motion sequence, such as a golf swing. The monitored aspects can include motion properties of an object moved by the user, position properties of the user and motion properties of the user. A data processing system for receiving data of the monitored aspects provides feedback data that is provided to a feedback output device, such as a graphical display device or speaker, so that the user is provided with feedback regarding the repetitive motion sequence. In one particular embodiment, the user's performance is compared to a template of a prior performance, with feedback being provided regarding the differences.

Another prior art document is U.S. Pat. No. 6,778,866 disclosing a method and apparatus for teaching a person how to perform a specific body motion in a consistent manner is based on electronically measuring one or more parameters of an actual body motion, comparing the one or more measured parameters with corresponding parameters of a target body motion, and providing a sensible feedback to the user based on a degree of correspondence between the one or more measured parameters and the corresponding target parameters. In a particular embodiment, the feedback is audible. More specifically the feedback is a musical tune that has a particular characteristic (such as rhythm) that is particularly suited to a particular body motion (such as a golf swing). The feedback may be in the form of electronically causing the musical tune to go off-key in proportion to a discrepancy between the actual body motion and the target body motion.

A further prior art system and method for teaching ergonomic motion of an athlete, for example a golfer is disclosed in WO200518759. The system including the video camera for capturing successive image of the golfer executing a preferring golf swing and a threshold definition system that allows the golfer define a spatial region of the video image. If the spatial region is intruded upon, an alarm is actuated, thereby providing feedback so the golfer may alter the technique of the next attempted motion. For example, the golfer may define the region such that if the club moves off plane during a swing, a tee removal system causes the ball to disappear. In this manner, the golfer is only able to hit the ball when the club stays on plane

SUMMARY OF THE INVENTION

The inventors have realised that a person trying to improve a complex movement such as for example a golf swing, a baseball bat stroke, a pole vault, or a discus throw often have problems to correct the faulty portions of the motion, and to replace these faulty portions with more effective ones. Also, the person's coach, even though equipped with advanced training aids such as video recording equipment may find it difficult, and/or time consuming to help the person improving his or her motion Traditional video recording of an athlete's movement is of help, but need to be studied afterwards, when the movement is completed and the video device has been set to playback, and do not provide such fast feedback as may be desired. A video recording also has to be studied and processed using the cognitive function of the human brain. It may be an advantage to provide feedback instead, or also, using the more non-cognitive functions of the brain, such as the emotional functions or reflexes.

The proposed training aid of the present invention enables the user to learn new movement patterns also on a subconscious level that creates learning free from the conscious analytical mind. This in turn makes the new movement pattern sustainable under pressure In order to overcome the drawbacks of prior art, the present invention provides a movements training aid, based on a small, lightweight sensor unit, attachable to a person's body, the sensor unit is able to provide sensor data that enables determining of the sensor unit's position relative to a reference position. Further, the body motion tracker comprises a processor unit configured to calculate and track the sensor unit's position. Still further the processor is configured to be able to compare the track in progress with a reference track provided in advance, to indicate a deviation.

Such deviation is then detected and indicated with almost no delay. The inventors have realised, in the course of trying to provide a fast feedback, that a video motion analysing machine may not be fast enough and that a system may be built at a comparatively lower cost if small unit such as a single chip motion tracking device could be adapted and configured to keep track of the motion in question.

According to a first aspect, the present invention provides a sports training aid comprising a sensor unit, the sensor unit being configured to be attachable to a user's body or a user's sports implement, and wherein the sensor unit is provided with:

a motion sensor module;

a feedback stimulator or means for wirelessly communicating with a feedback stimulator;

a processor; wherein the sports training aid is configured to provide real time feedback related to a motion fault of a studied sports motion performed by the user, and i) wherein the sensor unit is intended to be attached to a user's body or a user's sports implement at a representative location, the representative location being bound to travel a path representative of the studied sports motion, and ii) wherein the motion sensor module of the sensor unit comprises acceleration sensors and gyro sensors, and iii) wherein the processor of the sensor unit is configured to determine, with the aid of data from the motion sensor module, a still position corresponding to an event wherein the sensor unit is determined to be still, and iv) wherein the processor is configured to keep track of the movements of the sensor module of the sensor unit relative to the still position, and v) wherein the processor is configured to activate, in real time, the feedback stimulator upon real time detection of a sports motion fault of the studied sports motion of the user as represented by the motion path of the motion sensor module of the sensor unit.

The training aid is configured to perform an initiation sequence setting internal position registers and velocity registers to zero upon receiving a trigger signal and/or detecting a predetermined event wherein the detecting of the predetermined event is the detecting of null or very limited motion during a predetermined first time period.

Further, the processor is configured to detect a still position to perform a coordinate system fixation. Still further, the processor is configured to detect motion start by identifying certain parameters.

BRIEF DESCRIPTION OF THE DRAWINGS

Non-limiting embodiments of the invention will now be described with reference to the figures in which:

FIG. 10a shows a graphical representation of measurements to detect a swing fault.

FIG. 10b shows a further graphical representation of measurements to detect a swing fault.

FIG. 10c shows a diagram of distance between back- and downswing as a function of downswing angle.

DETAILED DESCRIPTION

Figure 1A:
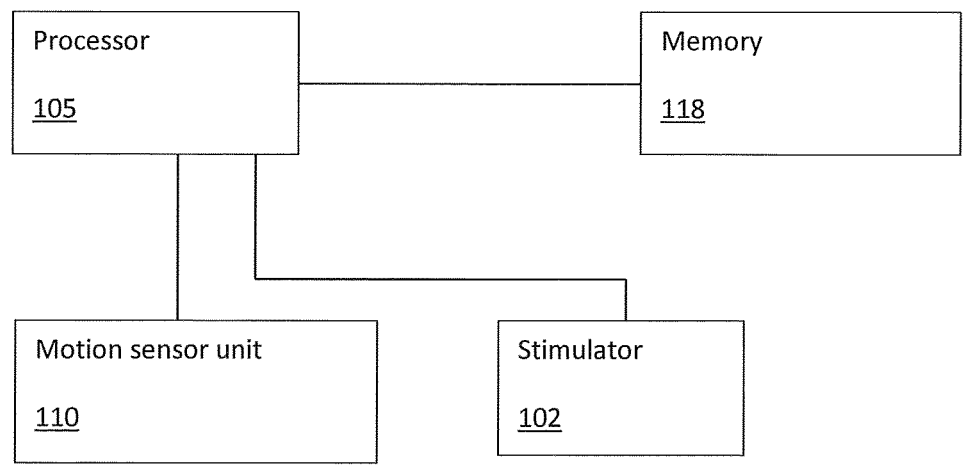
FIG. 1a shows a block diagram of a biofeedback device according to an embodiment of the present invention.

Definitions For the purpose of the present invention, and in the following text, the following terms are used with the meaning as explained below.

"Motion": With the term "motion" is understood any body movement, performed by a user, composite or simple, may it be a movement of one or more of his or her extremities, or torso, or centre of gravity. Any possible ambiguities should be solved by the context in which the term is used. Example motions include, but are not limited to, portions of or complete high jumps, pole vaults, hammer throws, javelin throws, gymnastics, choreography moves, cheerleading moves, baseball battings, baseball pitching, golf swings, putting strokes, or horse jumps. In various embodiments motion also includes rotational movement.

"Motion representation": A "motion representation" is a usually mathematical representation of a motion. The motion representation may include representations of linear and rotational motion position, motion velocity, and motion acceleration. For example, the motion may be represented by the current position of a predetermined point on the body of a user, or the motion may be represented by a (motion) track, see below.

"Position": With the term "position", as used herein is understood the physical local position of a sensor unit or small object in relation to a nearby reference point and expressed using a suitable coordinate system. Typically, in the context of the present invention, positions are within the magnitude of 0-5 meters from the reference point.

"Undesired motion": The term "undesired motion" is used to denote a motion that is undesired or comprises an undesired feature as seen from the point of view of the user, and/or his or her coach.

"Body motion tracker": As used herein, the term "body motion tracker" denotes a device or a system, or a piece of computer code when executed capable of tracking one or more predefined points of a user's body over time, based on processed sensor data.

"Tracking": With the term "tracking" is understood the activity of collecting and storing (recording) consecutive positions of one or more predefined points on a user's body during a motion.

"Motion track": With the term "motion track" is meant the result of the tracking activity, i.e., the collective amount of stored consecutive positions of a predefined body point over time, starting at a start point or start time, and ending at a finishing point or finishing time.

"Reference motion track": A "reference motion track" is a desired motion track that can be used to create a model to which motion representations of motions can be compared.

"Rotation angle" or "Angle of rotation": In two-dimensional space the "angle of rotation" is a measurement of the amount, the angle, by which an object is rotated about a fixed point. In three-dimensional space rotation is measured and indicated using angles of rotation about three coordinate axes.

"Predefined body point": With the term "predefined body point" is meant a point on a user's body that has been provided with means for facilitating the tracking of said point, e.g. a sensor unit.

"Attitude": In the context of the present invention the term "attitude" is used to denote an object's orientation (attitude, angular position) in space. The attitude may be represented by pitch, yaw and roll angles or, alternatively, by an attitude vector or axis, and a rotation angle around that vector or axis, i.e. axis-angle representation, cf. Euler's rotation theorem.

"Motion sensor unit": A "motion sensor unit" is understood to be a unit, attachable to a user's body, that are able to deliver motion information, such as accelerations, and/or gyroscopic data, i.e., information making it possible to determine the sensor's attitude and three-dimensional position or changes in the same position during a motion of the user, in a suitable reference system. The sensor unit is conceived to be small and lightweight enough not to interfere with the motion of the user.

"Control unit": In the context of the present invention a "control unit" is a unit comprising a man-machine interface for operating a device, it also usually comprises wireless communication means to communicate with the processor and/or the motion sensor unit.

"Sample": In the context of the present invention the term "sample" is used to denote a calculated state of the motion sensor unit at a particular moment in time and may include representations of linear and/or rotational: motion position, motion velocity, and motion acceleration as calculated by the processor based on motion sensor data from the motion sensor unit and also based on a reference frame, i.e., a coordinate system. Associated with the sample are a sample number and/or a sample time.

"Processor": In the context of the present invention the term "processor" is used to denote a processor system irrespective if it comprises one or more logical or physical processors, if nothing else is explicitly mentioned.

"Memory": In the context of the present invention the term "memory" is used to denote a memory system irrespective if it comprises one or more logical or physical memories, if nothing else is explicitly mentioned "Stimulator": In the context of the present invention the term stimulator is used to denote a device, attachable to a body of a person or animal, and upon receiving a command, capable of eliciting a stimulus perceptible by that person or animal.

FIG. 1a shows a block diagram of a training aid system according to an embodiment of the present invention. The training aid system comprises a motion sensor unit 110 for providing motion sensor data. The motion sensor unit 110 is configured to be easily attachable to a body part of a person or to an implement used by said person. It could be in the form of e.g. a bracelet or a plaster. The motion sensor unit 110 is connected to a processor 105 configured to process motion sensor data, and to a memory 118.

Figure 1B:
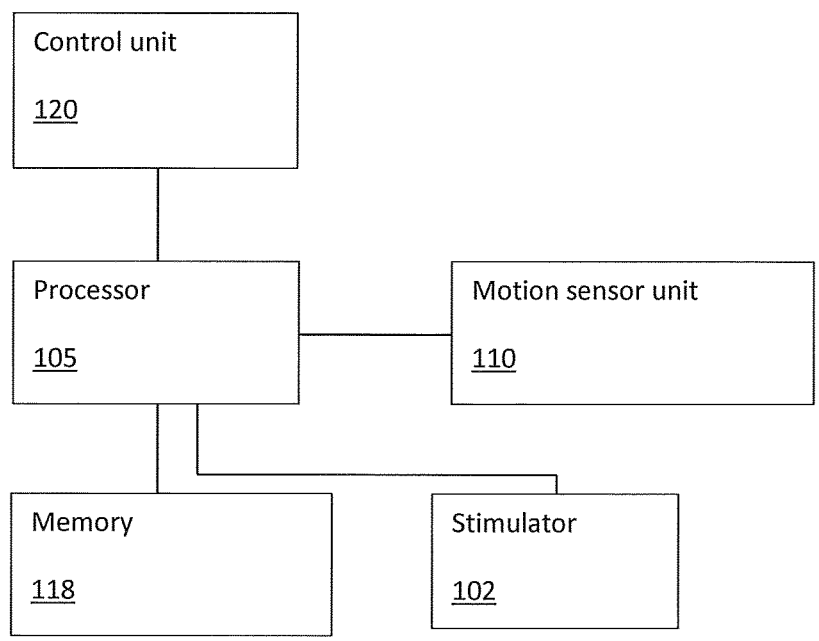
FIG. 1b shows a block diagram of a biofeedback device according to another embodiment of the present invention

The system may further comprise a control unit 120 for easy communication with the processor 105, FIG. 1b. The control unit is preferably handheld. The processor is connected to a memory 118 for storing of data. Further, the system comprises a stimulator 102 capable of eliciting a stimulus perceptible by the person. The stimulator 102 is preferably attachable to the body of the person. Preferably the stimulator 102, the processor 105, the memory 118 and the motion sensor unit may all be arranged or integrated in the same physical unit.

Figure 4D:
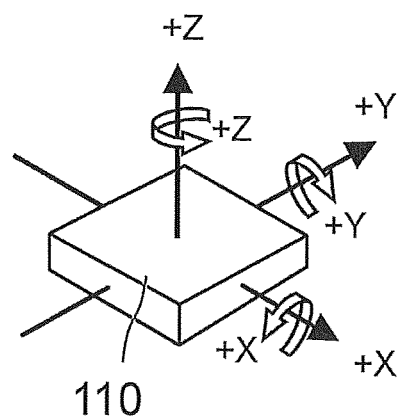
FIG. 4d shows a schematic perspective view of a motion sensor unit with reference directions for accelerometer and gyro data.
Figure 4D:
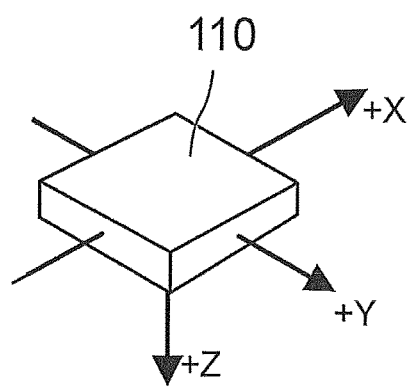
Figure 4A:
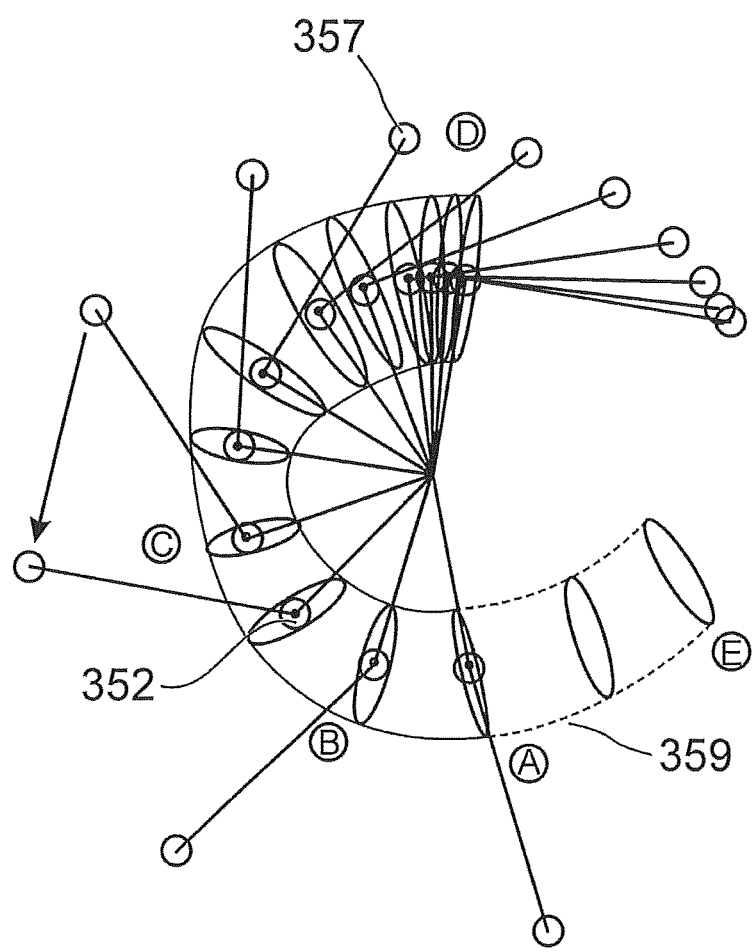
FIG. 4a shows a schematic representation as seen from above of a golf swing as consecutive positions of the club and wrist superimposed together with a tube of allowed deviation.

Thus, the motion sensor unit 110 is provided with one or more sensors capable of providing motion data to the processor 105 to which it is connected, and the processor 105 are configured to keep track of subsequent three-dimensional positions of the motion sensor unit 110. The motion sensor unit may preferably be a small single chip motion tracking device providing accelerometer and/or gyroscopic data allowing the processor to calculate relative position data of the motion sensor unit without the need for external references. An example of reference directions of a 9-axis motion sensor unit is shown in FIG. 4d. Accelerations are provided for X, Y, and Z-axis directions and also rotational accelerations around said axes respectively. A commercially available unit is the semiconductor motion tracker device MPU-9250 from INVENSENSE, San Jose, Calif.

Wireless Communication The system may further comprise wireless communication means, e.g. Bluetooth or WIFI enabling the processor 105 to communicate with the control unit 120.

Modes In various embodiments the control unit can be used to set the system in one out of two modes, a threshold set mode and a supervision mode:

in the threshold set mode a first three-dimensional track can be defined together with a threshold, also called allowable deviation which may be any limit or threshold associated with the motion, including, but not limited to a radius of a virtual tube created with a reference motion track as centre axis. Also, attitude deviation parameters can be set in this mode.

Figure 4B:
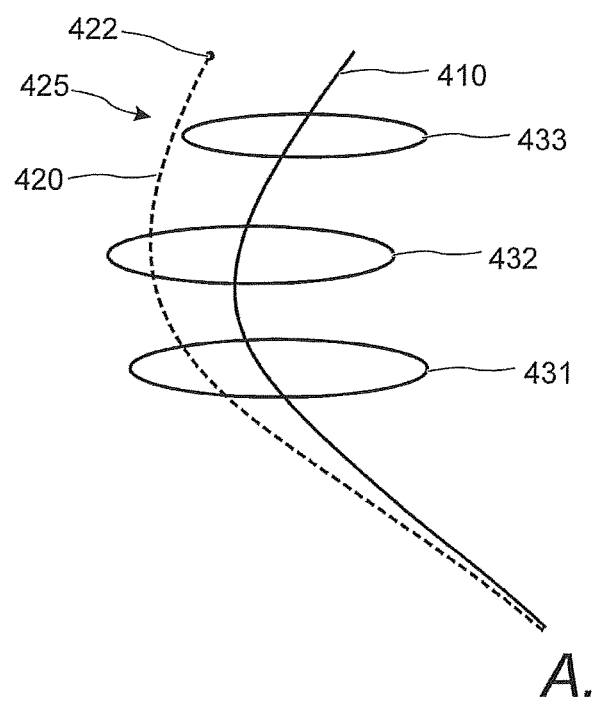
FIG. 4b shows a detail of a virtual tube of allowed deviation.
Figure 4C:
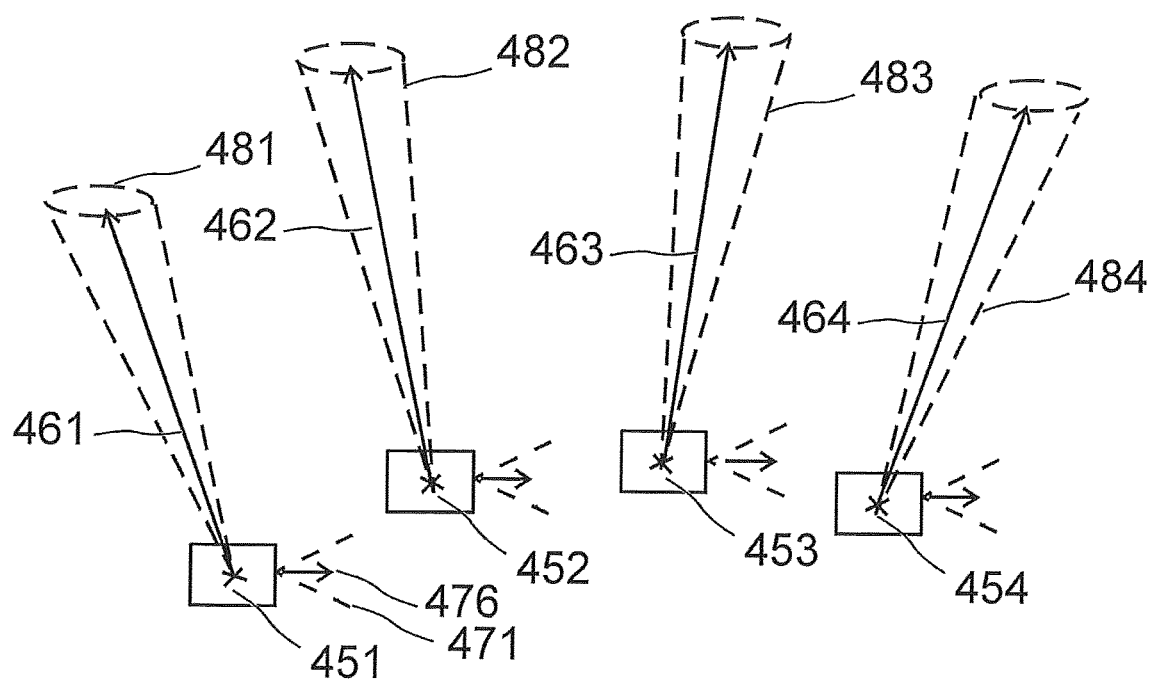
FIG. 4c shows a few sample points of a motion together with directional vectors of each point and limit cones/sectors for the directional vectors.

Further, the system is configured such that it is possible to connect the control unit to the Internet and import a reference motion track and an allowable deviation. The control unit is also configured to facilitate adjustment of parameters of allowable deviation. Typical parameters of allowable deviation may include radius, measured from a centre curve 410, of an allowable tube 431, 432, 433, see FIG. 4b, and allowable attitude deviation angle(s) represented by cones of allowable attitude angles, and/or attitude angle intervals, see FIG. 4c. In various embodiments a desirable track, and/or desirable attitude angles may be predefined as a factory setting that may be adjusted by input of certain body measurements, such as e.g. fingertip to ground distance, and arm length, depending on motion to be practiced (trained).

In the supervision mode, the processor is configured to compare either the sensor unit position, or both sensor unit position and sensor unit attitude, with reference values. Regarding position, as long as the actual movement stays within the virtual tube, the motion is considered satisfactory and no stimulus will be elicited. Thus, depending on the motion sensor unit 110 movement relative to certain limits or thresholds or a reference movement, the processor may immediately send, to the stimulus unit 102 a command to elicit a first stimulus, when the motion sensor unit has moved away outside any limits or thresholds or away further than the allowable deviation distance and/or the attitude has deviated outside an angular cone.

In various embodiments the processor may be configured to accomplish a comparison with a predetermined motion only and is not configured to be able to be set in any threshold or reference motion modes.

Stimulus Type In various embodiments, the system is provided with a stimulator 102 to elicit a stimulus depending on the current motion compared to a reference motion or to specific motion criteria. The stimulator 102 is preferably configured to provide a discouraging stimulus. The stimulus may be a tactile stimulus, electrical stimulus, light stimulus, auditory stimulus, heat stimulus, or cold stimulus, or a combination thereof. Depending on the needs of the user the stimulus can be selected to maximize motor learning. Preferably the stimulus elicited by the stimulus unit is an electric stimulus. Even more preferred, the stimulus unit is configured to be able to elicit an electric stimulus of such magnitude that it is perceived as painful to most humans. The stimulus unit is configured to be able to deliver such stimuli. The system may be configured such that the magnitude of the stimulus is adjustable.

The stimulus unit is configured to deliver the stimulus in real time, i.e., without noticeable delay, preferably with less delay than 50 milliseconds (ms), or more preferred less than 20 ms, or most preferred less than 10 ms.

Figure 2A:
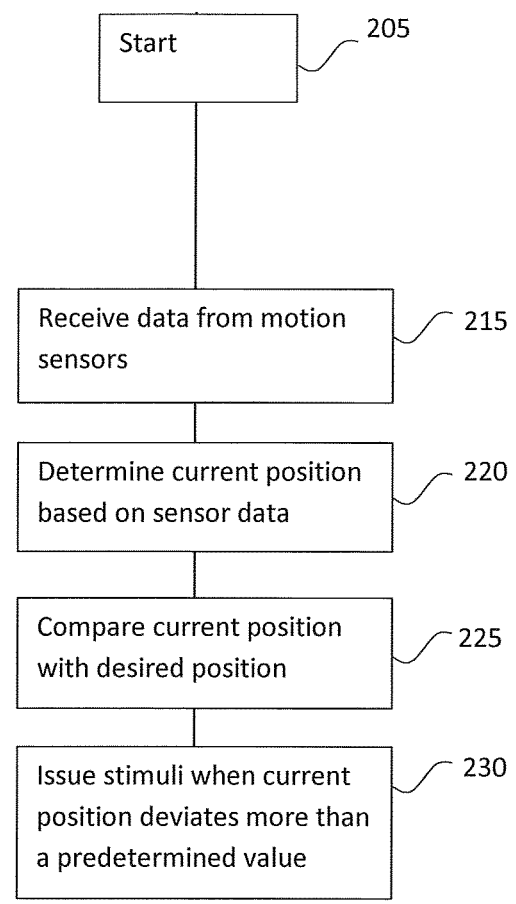
FIG. 2a shows a flow chart of a method for providing biofeedback to a person on a body motion.

Method For Training Correct Position Now referring to FIG. 2a, there is provided a method for a training aid for a person or animal provided with a motion sensor unit 110, in order to improve a body motion, the method comprising the steps of receiving 215 motion sensor unit 110 data;

determining 220 the current position of the sensor unit based on sensor unit data;

comparing 225 the current motion position values of the sensor unit as determined with corresponding position values of a predetermined desired motion, or with specific motion criteria;

issuing 230 a stimulus based on the level of disagreement between the position values of the current motion and of the predetermined desired motion, in view of a predetermined threshold value, or based on specific motion criteria; wherein the stimulus issued may be an electrical stimulus.

Figure 2B:
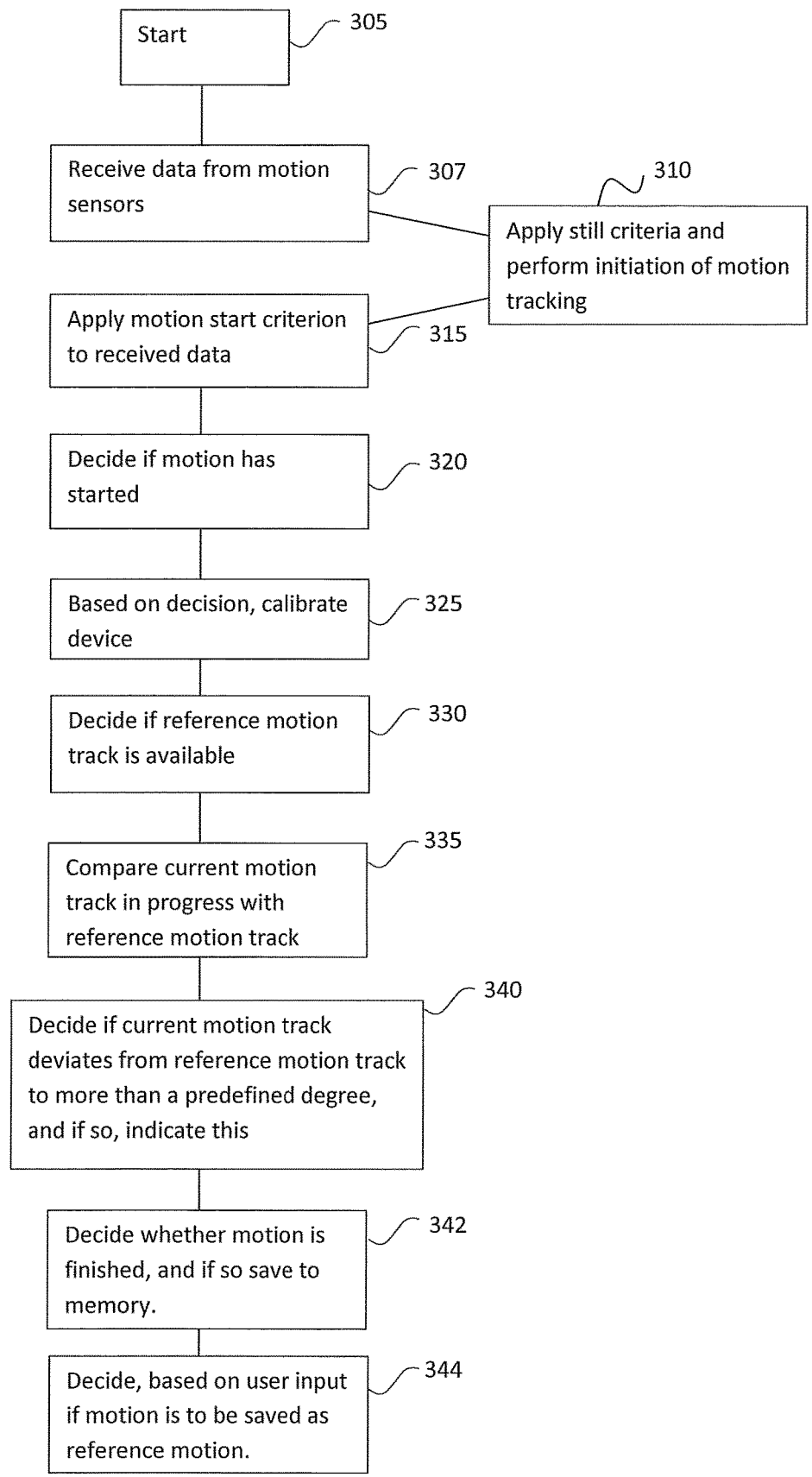
FIG. 2b shows a flow chart of another method for providing biofeedback to a person on a body motion.
Figure 3A:
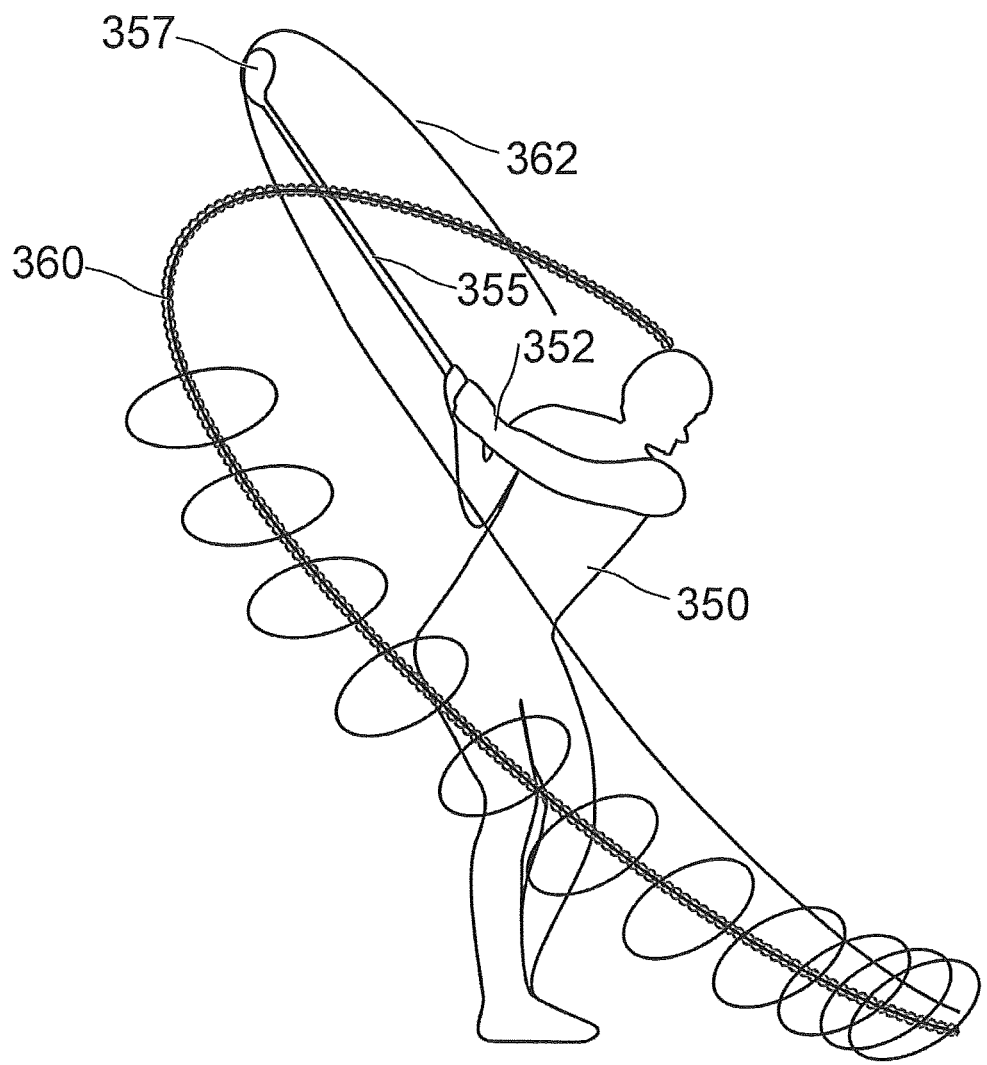
FIG. 3a shows a perspective view of a golfer swinging a club
Figure 3B:
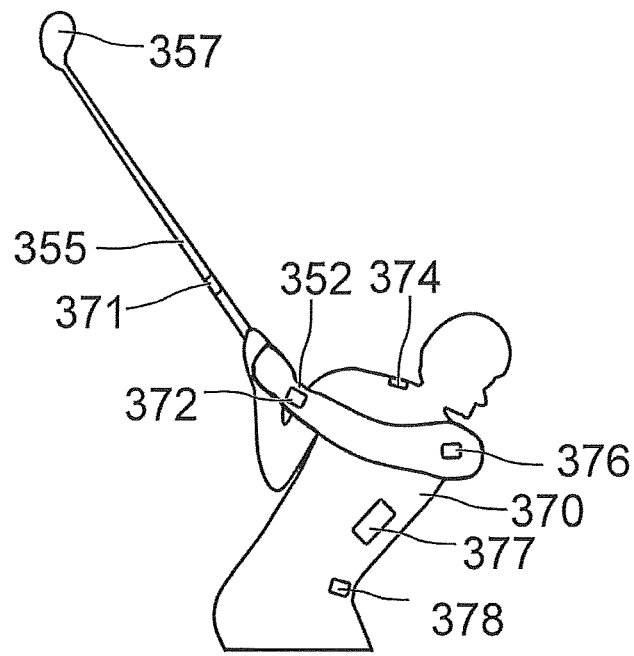
FIG. 3b shows a perspective view of an athlete's body with attached devices.

Now referring to FIG. 2b, the method may comprise additional steps as illustrated. It is shown a flow chart of another method for providing biofeedback to a person on a body motion, the method comprising the steps of initiating (306) internal motion registers for sensor unit position, velocity and attitude, see also paragraph below;

receiving 307 data from motion sensors;

applying 315 motion start criterion to received data, see below;

deciding 320 if motion has started;

calibrating 325 device based on decision of step 320, see below;

deciding 330 if reference motion track is available;

comparing 335 current motion track in progress with reference motion track;

deciding 340 if current motion track deviates from reference motion track to more than a predefined degree, and if so, indicate this;

deciding 342 whether motion is finished, and if so save to memory;

deciding 344 based on user input if motion track is to be saved as a reference motion track.

Initiation In various embodiments the training aid is relying on accelerometer and gyroscopic data from a MEMS motion tracking device. The processor is configured to have internal (to the processor) or external position registers, attitude registers, and velocity registers for keeping updated the current position, attitude and velocity of the motion sensor unit. The registers are updated using motion sensor data from the motion sensor unit. The processor is configured to perform an initiation procedure to reset position coordinates of the position of the motion sensor unit. In various embodiments initiation of registers is done by keeping the sensor unit still for a predetermined amount of time.

The inventors have identified the problem of creating a fast and accurate enough way of determining motion parameters to be able to detect a faulty motion in real time. The solution must cope with a two-step integration procedure to calculate position based on acceleration type data, which position may be associated with a more or less random amount of drift. Their solution to the problem includes the initiation procedure mentioned above and further detailed below. It is performed directly before motion analysis commence, and in a certain way to minimize any drift.

During research it was found that one important parameter to determine is the orientation of the sensor unit relative to the direction of gravity acceleration. During a period of keeping the sensor unit still, the sensor unit determines the orientation of the sensor unit in relation to the gravity acceleration vector. The orientation of left-right, and forward-backward directions is arbitrary set except for being perpendicular to gravity, and further calculations are configured accordingly.

Thus, initiation may preferably be done by pressing a button on the motion sensor unit or the control unit and/or by keeping the sensor unit "still" for a predetermined amount of time, and/or just by keeping it still enough, i.e., so still that activity level of accelerometer and gyro is below certain levels.

The predetermined time period may preferably be between 1 to 5000 milliseconds in duration, or more preferred between 5 to 20 milliseconds in duration, or even more preferred between 7 and 15 milliseconds, or most preferred between 9 and 11 milliseconds, during which time period the processor preferably averages received motion sensor data (accelerations) and if the average is below a certain value, the processor determines (decides) that initiation can proceed.

Thus, during the initiation procedure the processor determines an initiation point in time upon receiving a trigger signal and/or detecting a predetermined event. The initiation point in time may be the moment in time wherein it is assessed that the sensor motion unit is not influenced by any acceleration apart from gravity.

The processor is configured to have internal (to the processor) or external position registers and velocity registers, these registers are set to zero at that initiation point in time or are updated to a current position and current velocity, based on motion sensor data and the notion (conception, idea, fact) that the registers were reset to zero (x, y, z)=(0, 0, 0), ($\dot{x}$, $\dot{y}$, $\dot{z}$)=(0, 0, 0) at that particular time.

Motion Start Identification

In various embodiments, the processor is preferably configured to search for a motion start identifier, i.e., a short motion sequence, or a predetermined attained speed of motion, betraying (telling, signalling) that motion has started. The direction of the start sequence may be determined as the direction of a velocity vector at a predetermined absolute value of the attained velocity of motion of the motion sensor unit. This direction is the used to align reference motion track with current motion, a process here also referred to as "calibration".

Figure 4E:
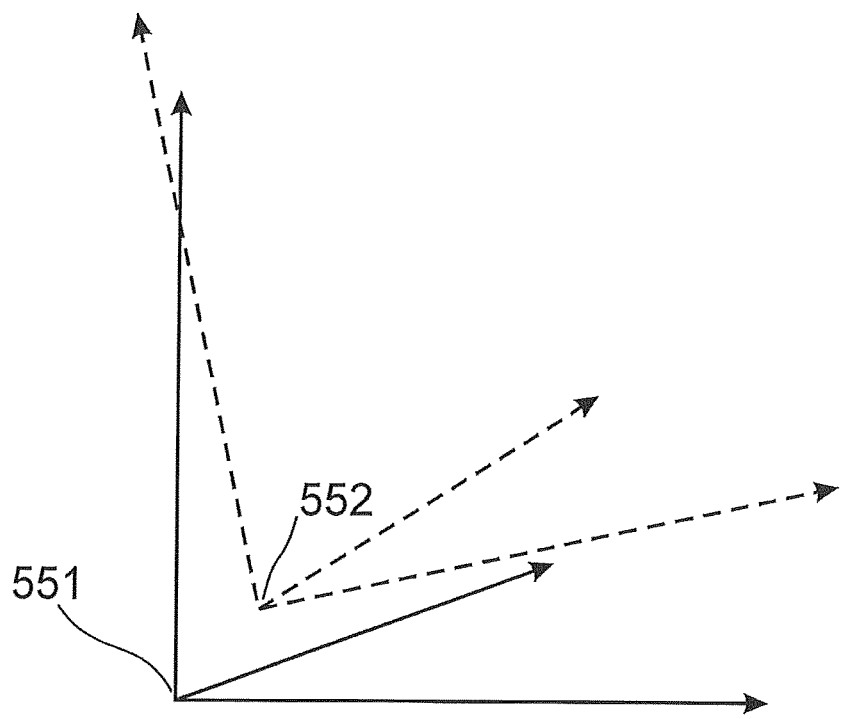
FIG. 4e shows a diagrammatic representation of two coordinate systems
Figure 4F:
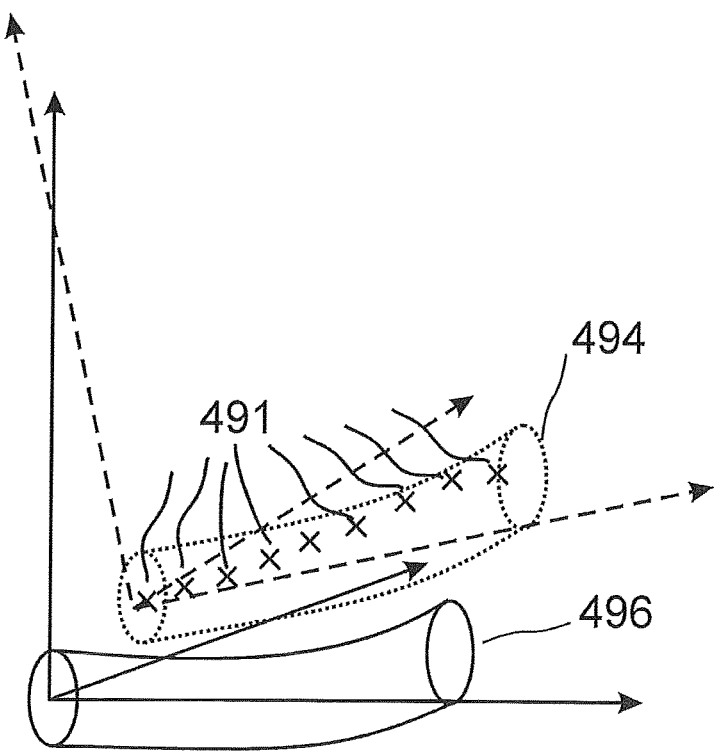
FIG. 4f shows the reference frames of FIG. 4e ready to be aligned using a motion start sequence or a still detection method.

FIG. 4e shows a schematic view of two different reference frames/coordinate systems. FIG. 4f shows the reference frames of FIG. 4e ready to be aligned. The processor is preferably configured to search for a motion start identifier, i.e., a short motion track portion (491). The processor is configured to align the short motion track portion (491) to fit in a virtual motion start tube 494. Subsequently the virtual motion start tube 494 is used to align the current reference frame having a second origin 552 to a reference motion reference frame having a first origin 551.

Another motion start identifier may be a predetermined attained speed of motion, signalling that motion has started and in what direction. The direction of the start sequence is preferably determined as direction of velocity vector at a predetermined absolute value of the attained velocity of motion of the motion sensor unit. This direction is then used to align reference motion track with current motion, as process here called calibration.

EXAMPLES OF INITIATION

In various exemplary embodiments there is provided a sports training aid comprising: a sensor unit, the sensor unit being configured to be attachable to a user's body or a user's sports implement, and wherein the sensor unit (110) is provided with:

a motion sensor module;

feedback stimulator or means for wirelessly communicating with a feedback stimulator;

a processor; wherein the sports training aid is configured to provide instantaneous feedback related to a motion fault of a studied sports motion performed by the user, and i) wherein the sensor unit is intended to be attached to a user's body or a user's sports implement at a representative location, the representative location being bound to travel a path representative of the studied sports motion, and ii) wherein the motion sensor module of the sensor unit comprises acceleration sensors and gyro sensors, and iii) wherein the processor of the sensor unit is configured to determine, with the aid of data from the motion sensor module, a still position corresponding to an event wherein the sensor unit (110) is determined to be still, and iv) wherein the processor is configured to keep track of the movements of the sensor module of the sensor unit relative to the still position, and v) wherein the processor is configured to activate, in real time, the feedback stimulator upon real time detection of a sports motion fault of the studied sports motion of the user as represented by the motion path of the motion sensor module of the sensor unit.

In various embodiments the processor is configured to determine the still position using a method including the following steps:

calculating repeatedly an acceleration vector based on data from 3-axis accelerometer sensors;

determining that the absolute value of the acceleration vector stays below a predetermined threshold value for a predetermined amount of time;

determining that the accelerometer vector holds a steady absolute value equal or close to earth gravity acceleration for the predetermined amount of time;

Further, the processor may be configured to determine the still position using a method including the following steps:

determining that gyro sensor's readings are confined within certain predefined limit values.

In various embodiments the determining of a steady absolute value includes the following step(s):

checking that variation in accelerometer vector absolute value is within a predetermined interval preferably within +/− certain percentage from earth gravity acceleration.

The processor may in a preferred embodiment be configured to discard gyro sensor data when determining the still position.

The user may be an animal.

EXAMPLES OF USE OF MOTION SENSOR DATA TO CALCULATE POSITION OF SENSOR UNIT

As also described above, motion data from a motion sensor module includes accelerometer data and gyroscopic data. A number of position registers are set to zero during the initiation procedure where a still position is identified. The orientation of the motion sensor module is set to the average of the direction of acceleration, that is assumed to be originating from earth gravity and maybe some small random fluctuations due to normal minor involuntary muscular contractions.

In various embodiments, output from triple-axis gyroscope of motion sensor module includes digital-output X-, Y-, and Z-axis angular rates. Output from accelerometers include triple axis-accelerations.

In various exemplary embodiments there is provided a sports training aid comprising: a sensor unit, the sensor unit being configured to be attachable to a user's body or a user's sports implement, and wherein the sensor unit (110) is provided with:

a motion sensor module;

a feedback stimulator or means for wirelessly communicating with a feedback stimulator;

a processor; wherein the sports training aid is configured to provide instantaneous feedback related to a motion fault of a studied sports motion performed by the user, and i) wherein the sensor unit is intended to be attached to a user's body or a user's sports implement at a representative location, the representative location being bound to travel a path representative of the studied sports motion, and ii) wherein the motion sensor module of the sensor unit comprises acceleration sensors and gyro sensors, and iii) wherein the processor of the sensor unit is configured to determine, with the aid of data from the motion sensor module, a still position corresponding to an event wherein the sensor unit (110) is determined to be still, and iv) wherein the processor is configured to keep track of the movements of the sensor module of the sensor unit relative to the still position, and v) wherein the processor is configured to activate, in real time, the feedback stimulator upon real time detection of a sports motion fault of the studied sports motion of the user as represented by the motion path of the motion sensor module of the sensor unit, and vi) wherein an initial orientation of the sensor module is determined and set based on accelerometer data of motion sensor module, and accelerometer data of motion sensor module only, corresponding to the still position, and vii) wherein the further, dynamically changing orientation of the sensor unit, is determined based on angular rates from the gyroscope of the motion sensor module, and angular rates from the gyroscope of the motion sensor module only.

In various embodiments the processor is configured to determine the still position using a method including the following steps:

calculating repeatedly an acceleration vector based on data from 3-axis accelerometer sensors;

determining that the absolute value of the acceleration vector stays below a predetermined threshold value for a predetermined amount of time;

determining that the accelerometer vector holds a steady absolute value equal or close to earth gravity acceleration for the predetermined amount of time;

Further, the processor may be configured to determine the still position using a method including the following steps:

determining that gyro sensor's readings are confined within certain predefined limit values.

The predetermined amount of time may preferably be in the interval of 0.5 to 2.5 seconds.

Still Indicator

As an alternative, in various embodiments, a fixed period is replaced with a still detector and an indicator, indicating that the system now is ready to be used. The still detector evaluates sensor data to be able to tell when acceleration and/or gyroscopic parameters are below a certain threshold.

In various embodiments the determining of a steady absolute value includes the following step(s):

checking that variation in accelerometer vector absolute value is within a predetermined interval preferably within a certain percentage from earth gravity acceleration.

The processor may in a preferred embodiment be configured to discard gyro sensor data when determining the still position.

The user may be an animal.

In various embodiments the further, dynamically changing, position of the motion sensor module is calculated based on the calculated, dynamically changing orientation (attitude) of the motion sensor module, and corresponding accelerometer data of the motion sensor module.

EXAMPLE OF STILL DETECTION

Figure 5:
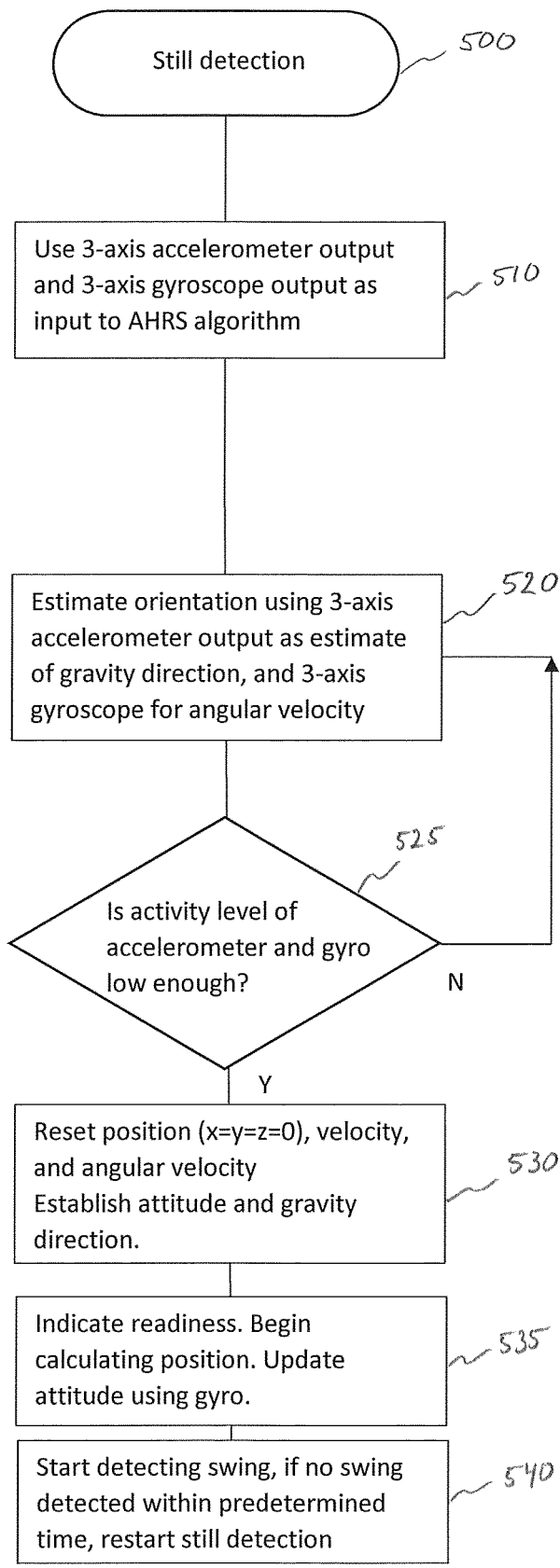
FIG. 5 shows a flowchart of a still detection method for establishing a reference position for training aid use.

FIG. 5 shows a flowchart of a still detector of a training aid. The aid is configured to perform a still detection 500 method including the following steps:

using 510 three-axis accelerometer output and 3-axis gyroscope output as input to an AHRS algorithm to determine orientation of a wrist sensor unit.

estimating 520, orientation using 3-axis accelerometer output as estimate of gravity direction, and 3-axis gyroscope for angular velocity;

determining 525, based on accelerometer and/or gyro activity level, if sensor unit is kept still enough;

reset 530 position to x=y=z=0;
reset 530 linear and angular velocity;
keep 530 attitude and gravity direction as adapted;
indicate 535 readiness, this may be done by showing a green light to the user;
begin calculating 535 and updating position;
updating attitude using gyro sensor data only;
start detecting 540 swing;
restart still detection 540 based on absence of swing within a predetermined time;

EXAMPLES OF GOLF SWING DETECTION

There is provided a golf training aid comprising a body unit attachable to a person's body wherein the body unit is provided with:
a positioning sensor module;
a feedback stimulator or means for wirelessly communicating with a feedback stimulator;
a processor;
wherein the golf training aid is configured to provide real time feedback, and wherein the body unit is intended to be attached to a person's body at a representative location, the location being bound to travel a path representative of the studied sports motion, and wherein the positioning sensor module comprises acceleration sensors and gyro sensors, and wherein the module is configured to keep track of the persons movements and to determine a still position wherein the body unit is determined to be still, and wherefrom acceleration and/or gyro signals can be used to determine the position of the body unit, and wherein acceleration sensor data only is used to determine orientation of body unit when still, and wherein gyroscopic data only is used to determine orientation of body unit when not still, and wherein the processor is configured to realize a golf swing detector arranged to detect that a golf swing is initiated, the golf swing detector may comprise inclusion criteria and rejection criteria, and wherein inclusion criteria comprises:

a height increase of at least a predetermined height increase within a certain time period from still, the certain time period preferably between 1.7 and 2.0 seconds, and the movement incudes an accumulated travelled angle of at least a predetermined amount, the predetermined amount being preferably within 100 to 120 degrees, more preferred around 110 degrees, and wherein rejection criteria comprises:

an initial still period unable to let the system determine a z-direction wherein the processor is configured to activate the feedback stimulator, upon detection of a sports motion fault of the person.

Further, the golf training aid may comprise that the predetermined height increase is in the interval of 0.4 to 0.6 meter, or more preferred between 0.45 and 0.55 m or most preferred between 0.49 and 0.51 m Still further, the golf training aid may comprise that the predetermined still threshold time is in the interval of 5 to 20 milliseconds, or more preferred in the interval of 7 to 15 milliseconds or most preferred 9 to 11 milliseconds.

EXAMPLE 3 "Golf Swing Training Aid"

There is provided a golf training aid comprising a sensor unit attachable to a user's body or a user's sports implement, wherein the sensor unit is provided with:
a position sensor module;
a feedback stimulator;
a processor;
wherein the sports training aid is configured to provide instantaneous feedback when a swing fault is detected, and wherein the body unit is intended to be attached to the person's body (or a person's sports implement) at a representative location, the location being bound to travel a path representative of the studied sports motion, and wherein the golf training aid comprises means to:
determine when the body unit is still, and
determine position of the body unit;
detect that a golf swing is initiated, and wherein an over-the-top detector arranged to signal when the person executes a golf swing with an over-the-top swing fault, the over-the-top detector comprising:
a processor; the processor being configured to calculate the position of a swing plane, based on position sensor data; the processor further being configured to calculate, in real time, the position of the body unit, relative to the swing plane, and to activate the feedback stimulator based on the path of the body unit relative to the swing plane being consistent with an over-the-top swing fault.

The golf training aid may further be configured such that the path of the body unit relative to the swing plane is considered being consistent with an over-the-top swing fault if the following criteria is fulfilled:

the downward portion of the body unit path is differing a distance A in front of the upward path in a direction perpendicular to the swing plane.

Determining a z-direction

In order to facilitate calculations and analysis of user movements, without the aid of an external reference, internal references are established using a procedure based on sensing the force of gravity during a period of voluntary inactivity, as introduced above.

The z-direction is defined as upwards, i.e., aligned with the direction of gravity, in a so called inertial frame, also known as a global frame. The sensor or sensor unit, which may be attached to the wrist of the arm, may be referred to as body frame, and the sensor need to constantly be able to determine or know how its coordinate system relate to the global frame. In various embodiments this is accomplished by the use of a so-called attitude and heading reference system (AHRS). Specific use of AHRS in mini-aerialvehicles is shown in: IEEE Transactions on automatic control, Vol. 53, No. 5, June 2008, p 1203 Mahony et.al.

The AHRS uses an AHRS algorithm to calculate the sensor orientation, i.e., not the sensor position, but merely its angle(s) in relation to global frame, also known as "attitude". The AHRS-algorithm is set to be active during the entire time, however it is configured to act differently depending on the user is still or is moving. During the still period the AHRS-algorithm uses accelerometer values as a reference for the direction of the gravitational force. The AHRS-algorithm adapt its orientation against the values of the accelerometer.

At the end of the still period the AHRS-algorithm has achieved the best possible estimate of the relationship between the body frame and the global frame. The AHRS algorithm is configured such that once the movement has started the accelerometer values is not used as a reference. This is done since during movement, accelerometer values comprise acceleration components caused by movements of the sensor. The AHRS-algorithm is configured to, during movement, to update sensor (unit) attitude and heading based on gyroscopic data only, and not using accelerometer data.

Setting X and Y Directions

The training aid is configured to internally use an x, y, z coordinate system to track and analyze the movement of the user as reflected by the movement of the sensor unit. The determining of the z-direction is described above. The x-, and y-directions in the global frame need not be determined in relation to a golf course or to a surrounding environment. However, internally, the user and the golf swing are rotated in the global frame such that a normal vector to a reference plane or "swing plane" (see below) projected on the x-y plane of the global frame is pointing in positive x-direction. This means that a launching direction of a golf ball is along the y-axis and that the nose of the golfer points along the positive x-direction.

Golf Training Aid

In various embodiments there is provided a golf swing training aid. The training aid may comprise features including a hardware or software to recognize the beginning of a golf swing. In various embodiments there is provided what the inventor(s) have chosen to call a "golf swing detector".

The first thing the golf swing detector is configured to do is to detect a progress from stationary to moving. This may be accomplished by setting a threshold value for one or more motion parameters and determine that a movement has started when one or more thresholds is/are exceeded. A progress from stationary to moving is happening each time the user moves after a stationary period.

The golf swing detector is further configured to return to wait for a new still period if nothing more happens within a predetermined period. This predetermined period may be set in the interval 1.5 to 2.5 seconds. If a movement of the sensor unit upwards, i.e, in the z-direction is detected, exceeding a predetermined distance, then the golf swing detector is allowed to carry on working. This predetermined distance may preferably be set to around 0.5 meter. In other words, motion in the x-y-plane together with movement upwards in z-direction can be seen as criteria for activating the golf swing detector.

Position Determining Hardware and Software

Figure 6:
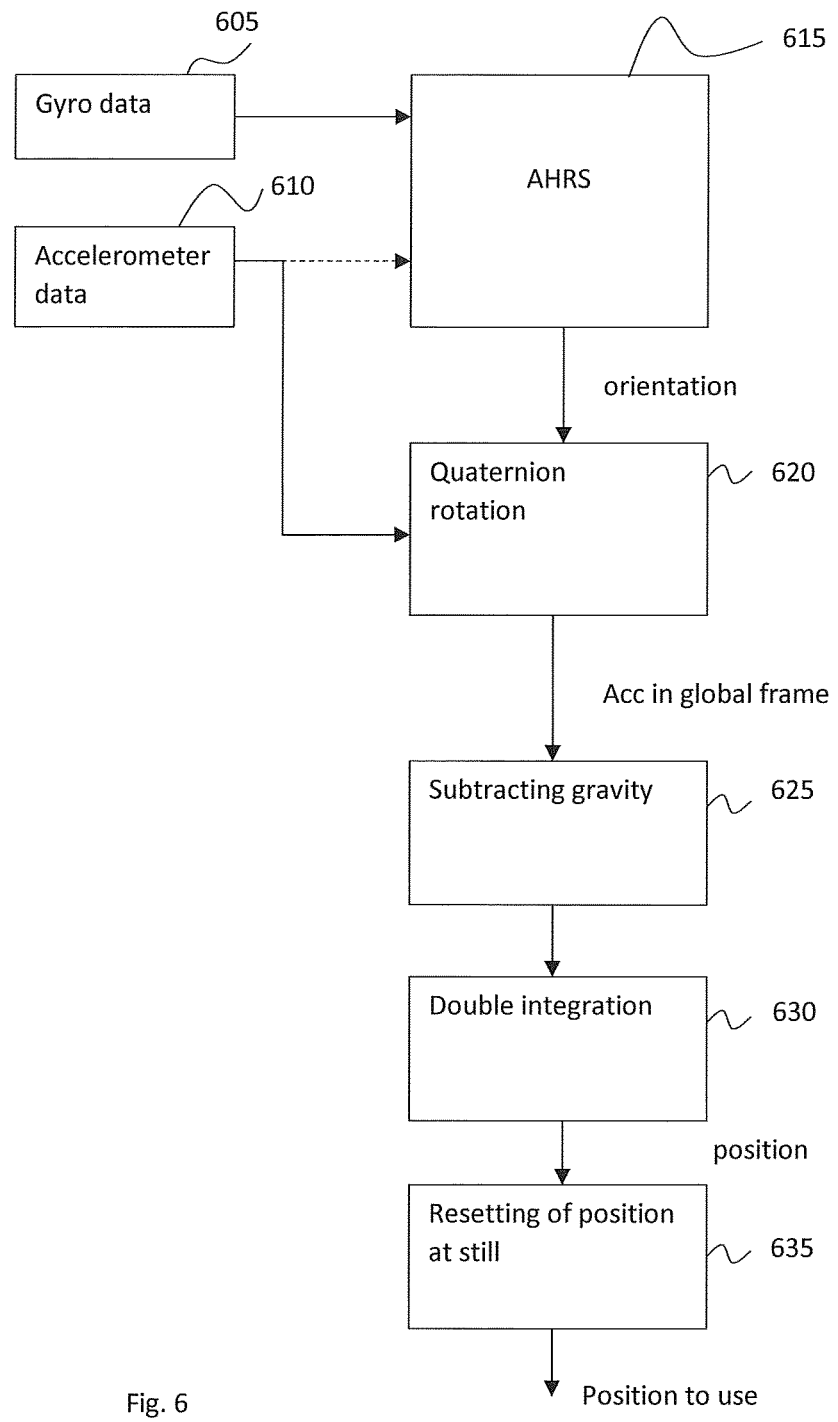
FIG. 6 shows a block diagram of a position calculation method for training aid use.

Now turning to FIG. 6, in various embodiments the position of the wrist sensor unit is determined by feeding an AHRS unit 615 with data from the wrist sensor units gyro data unit 605 and the sensor units accelerometer data unit 610. The AHRS unit feed orientation/attitude data to a quaternion rotation unit 620 which establishes and keeps track of local frame orientation in relation to global frame. The quaternion rotation unit provides acceleration data in global frame format to a subtracting gravity unit 625 which subtracts gravity component. Acceleration data is fed from the subtracting gravity unit 625 to a double integration unit 630 which in turn feeds position data. Resetting of position coordinates may be performed by a resetting unit 635.

Setting a Reference Plane

Figure 7A:
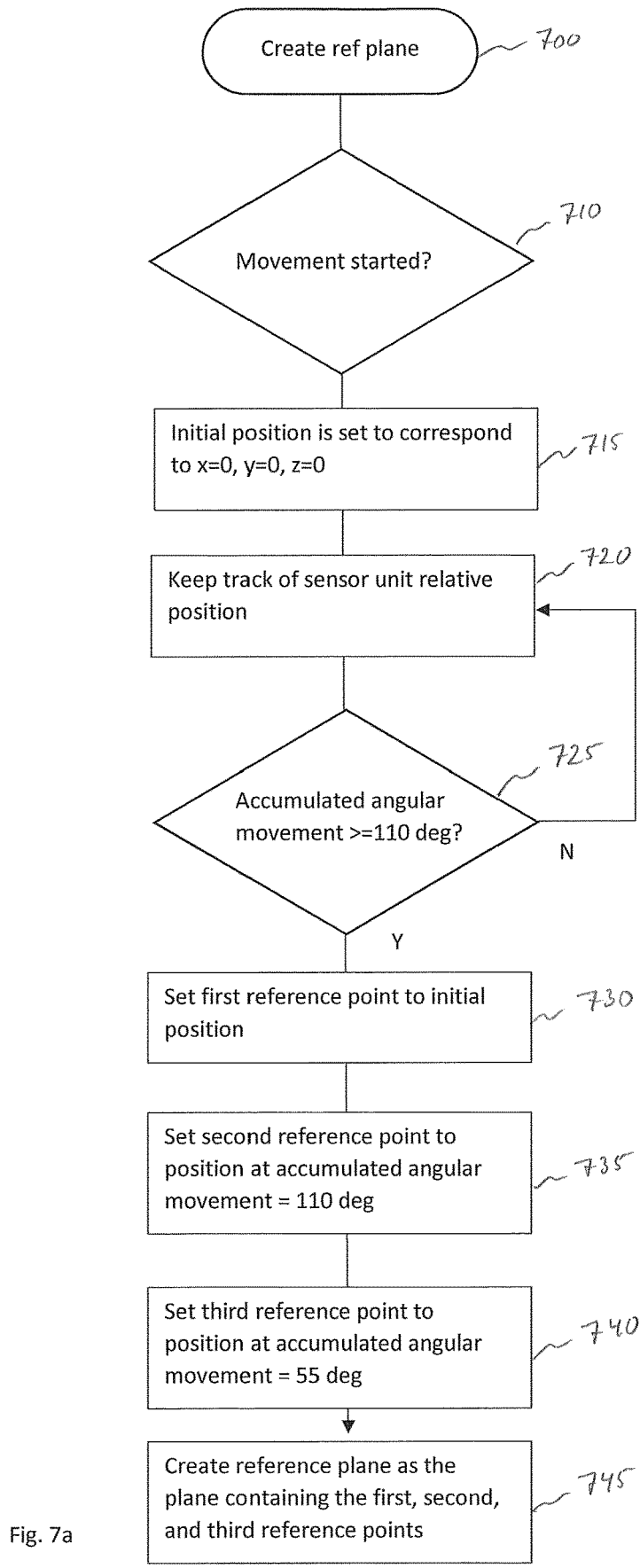
FIG. 7a shows a flowchart of a method for establishing a reference plane for training aid use.

In various embodiments the training aid is configured to determine a reference plane. This plane may also be referred to as a swing plane, but since this term is sometimes used with other meanings in golf literature, it is preferred here to call it a reference plane. FIG. 7a shows a flowchart of a method for establishing a reference plane for training aid use. The method comprises the following steps:

determining that a movement has started, i.e., determining that from a still position accelerometer and/or gyro data is consistent with a movement of the sensor unit;

setting 715 the initial position to the position immediately before the movement started to x=y=z=0;

keeping track 720 of sensor unit relative position determining 725 if gyroscopic accumulated angular movement (since still) is greater or equal to a predetermined value, likely to be a substantial part of a swing. Tests have shown that a suitable value is around 110 degrees;

setting 730 a first reference point to the initial position;

setting 735 a second reference point to the position at the predetermined accumulated angular value;

setting 740 a third reference point to the position at half the predetermined accumulated angular value;

creating 745 a reference plane as the plane containing the first, second and third reference points.

Thus, the reference plane being the plane defined by three reference points, wherein a first reference point may be the point where the sensor unit is at still, a second reference point may be the point where the sensor unit is when a predetermined value of a gyroscopic angular movement is attained, and the third reference point may be a point where the sensor unit is when the value of the gyroscopic angular movement is somewhere between the value at still and the predetermined value. Preferably about half way in between. In doing this, the gyroscopic angular movement value may be set to zero at still. Preferably the predetermined value is between 100 and 120 degrees, more preferred between 105 and 115 degrees, and most preferred 110 degrees.

Figure 7B:
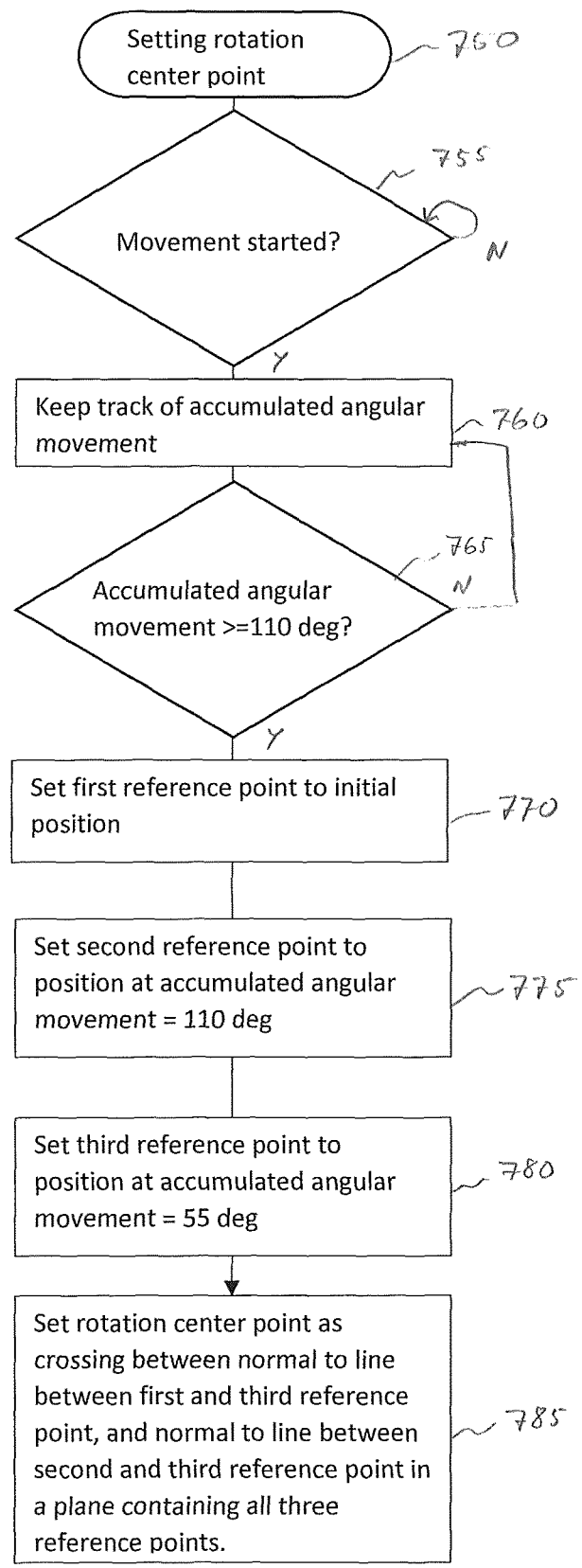
FIG. 7b shows a flowchart of a method for establishing a center point of rotation for training aid use.

FIG. 7b shows a flowchart of a method for establishing a center point of rotation for training aid use. The method comprises the following steps:

determining 755 that a movement has started, i.e., determining that from a still position accelerometer and/or gyro data is consistent with a movement of the sensor unit;

setting the initial position to the position immediately before the movement started to x=y=z=0;

keeping track of sensor unit relative position determining 765 if gyroscopic accumulated angular movement is greater or equal to a predetermined value, likely to be a substantial part of a swing. Tests have shown that a suitable value is around 110 degrees;

setting 770 a first reference point to the initial position;

setting 775 a second reference point to the position at the predetermined accumulated angular value;

setting 780 a third reference point to the position at half the predetermined accumulated angular value;

Setting 785 a rotation center point as crossing between normal to line between first and third reference point, and normal to line between second and third reference point in the reference plane described above.

Figure 8:
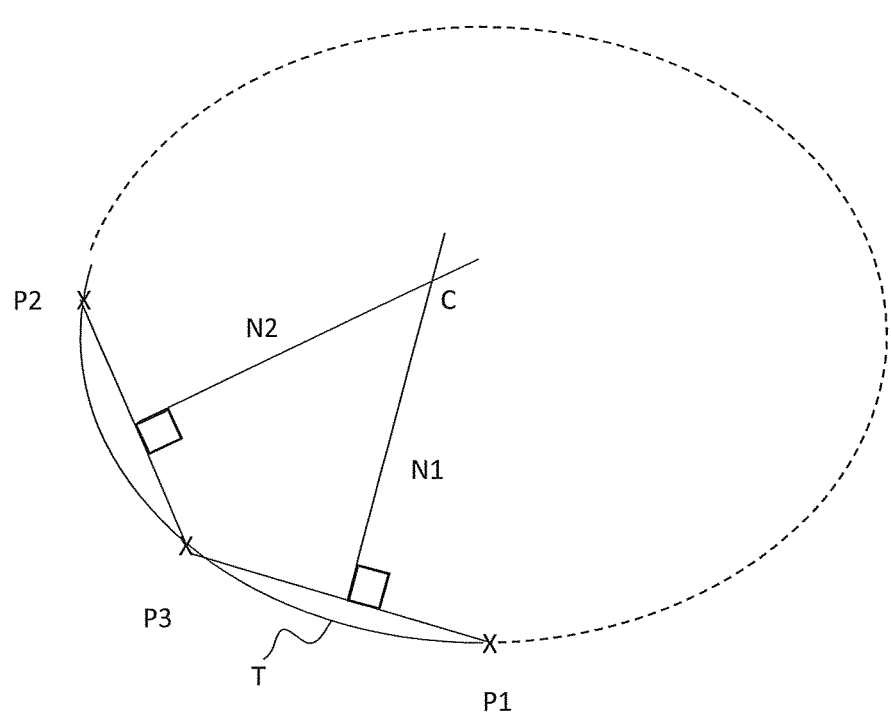
FIG. 8 shows geometrical relations relevant for the method of FIG. 7b.

FIG. 8 shows geometrical relations relevant for the method of FIG. 7b. P1 is first reference point. P2 is second, P3 is third reference point as in plane determined in FIG. 7a. The line P1-P3 is line between first and third reference point. P2-P3 is the line between second and third reference point. N1 is the normal to line P1-P3 originating from halfway between P1 and P3. N2 is the normal to line P2-P3 originating from halfway between P2 and P3. Rotational centerpoint C is marked C. T is the track.

Detecting an over-the-top swing fault

Figure 9:
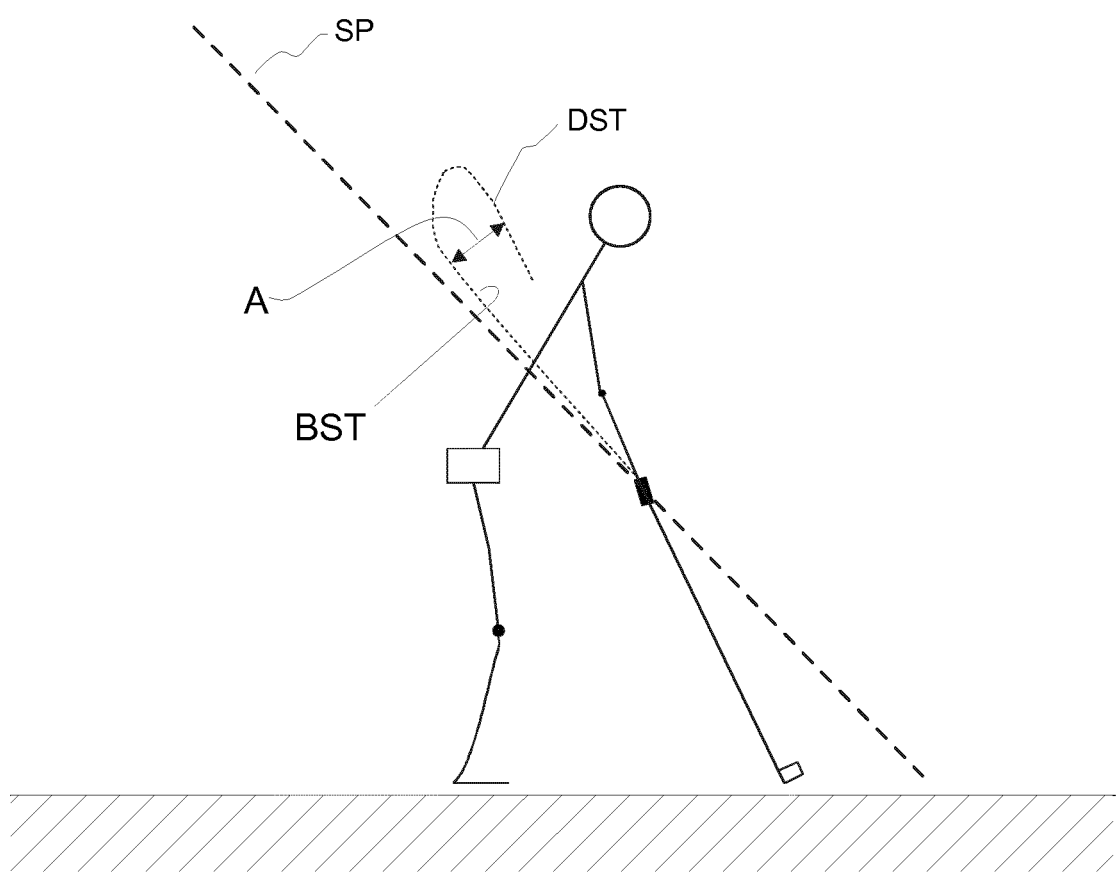
FIG. 9 shows a side view of a stick figure golfer.

FIG. 9 shows a side view of a stick figure golfer. A backswing track BST is shown as a dashed line marked BST. A downswing track DST is shown as a dashed line marked DST. A reference or swing plane is marked SP. A distance A between the backswing track BST and the downswing track DST is marked A.

FIG. 10a shows a graphical representation of measurements to detect a swing fault. A backswing track BST transitions to a downswing track DST at transition point "0". A first downswing angle beta1 is shown to be 10 degrees and a second downswing angle is shown to be 20 degrees FIG. 10b shows a further graphical representation of measurements to point out the measured distance A1 and A2 between backswing track BST and downswing track DST. TP is transition point. RPL is reference plane as seen from the side.

FIG. 10c shows a diagram of distance as a function of downswing angle. The dashed area is corresponding to criteria for detecting an over-the-top swing fault. Tests have shown that at certain downswing angles such as 20 degrees, a distance A between the backswing track and the downswing track in the direction of the normal to the reference plane, up and forward, is consistent with an over-the-top swing fault. In various embodiments this is used to trigger a stimulator to create negative feedback to the user, as also described earlier.

Figure 11:
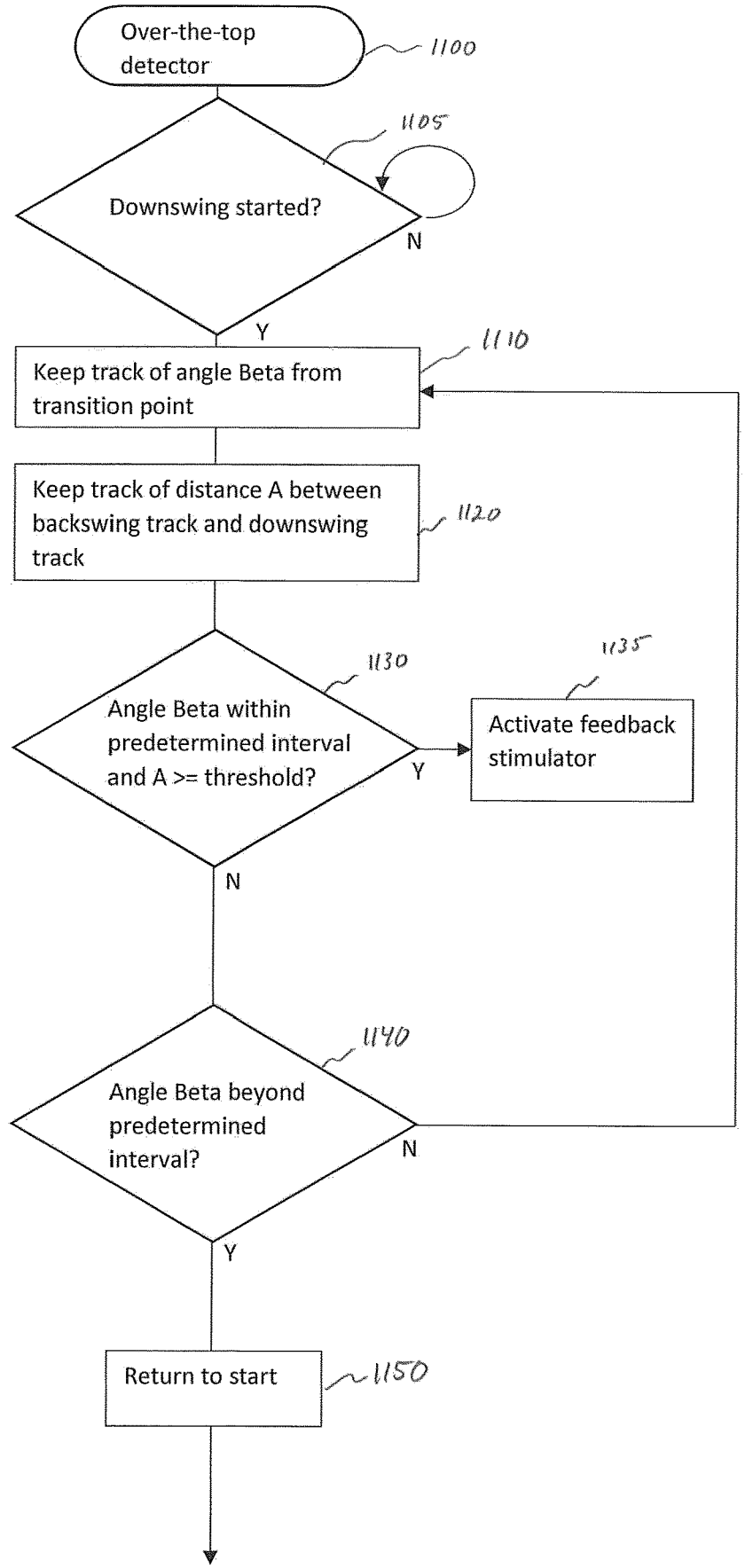
FIG. 11 shows a flowchart of an over-the-top swing fault detection method.

FIG. 11 shows a flowchart of an over-the-top swing fault detection method. The method comprises the following steps:
determining 1105 that the downswing has started, this may be done by detecting that the angle around the rotation center point is no longer increasing, but is decreasing;
keeping track 1110 of angle Beta (β) from transition point TP, cf FIG. 10a, 10b;
keeping track 1120 of distance A between backswing track BST and downswing track DST;
determining 1130 whether the downswing track is consistent with an over-the-top swing fault or not, by considering if angle Beta is within a predetermined angle interval at the same time as the distance A between the backswing track and the downswing track is within a predetermined distance interval. Tests have shown that suitable values include a predetermined angle interval of 10 to 25 degrees and the predetermined distance interval including a value over 2 cm.; The method may include the further following steps:
activating 1135 the feedback stimulator;
determining 1140 that angle Beta is beyond a predetermined interval;

In further embodiments, also an under-the-top (UTT) swing fault may be detected. This is calculated analogous to the OTT but the distance interval lay on the negative side. For example, minus (−) 10 cm in an angle interval of 10 to 25 degrees.

In further embodiments the processor may be configured such that the predetermined angle interval and the predetermined distance interval are self-adjusting.

The invention claimed is:

1. A sports training aid comprising:
a sensor unit, the sensor unit being configured to be attachable to a user's body or a user's sports implement, the sensor unit comprising:
a motion sensor module;
a feedback stimulator or means for wirelessly communicating with a feedback stimulator; and
a processor;
wherein the sports training aid is configured to provide real time feedback related to a motion fault of a studied sports motion performed by the user,
wherein the sensor unit is intended to be attached to a user's body or a user's sports implement at a representative location, the representative location being bound to travel a path representative of the studied sports motion,
wherein the motion sensor module of the sensor unit comprises acceleration sensors and gyro sensors,
wherein the processor of the sensor unit is configured to determine, with the aid of data from the motion sensor module, a still position corresponding to an event wherein the sensor unit is determined to be still,
wherein the processor is configured to keep track of the movements of the sensor module of the sensor unit relative to the still position,
wherein the processor is configured to activate, in real time, the feedback stimulator upon real time detection of a sports motion fault of the studied sports motion of the user as represented by the motion path of the motion sensor module of the sensor unit, the sports motion fault determined by the motion path of the motion sensor module deviating or not deviating from a threshold represented by a radius of a virtual tube, and
wherein the processor is configured to calculate an orientation and a position of a reference plane, based on sensor unit data, the reference plane being the plane defined by three reference points, wherein a first reference point is the point where the sensor unit is at still, a second reference point is the point where the sensor unit is when a predetermined value of a gyroscopic angular movement is attained, and the third reference point is a point where the sensor unit is when the value of the gyroscopic angular movement is between a value at still and the predetermined value.

2. The sports training aid of claim 1, wherein the processor is configured to determine the still position using a method including:
calculating repeatedly an acceleration vector based on data from the accelerometer sensors;
determining that the absolute value of the acceleration vector stays below a predetermined threshold value for a predetermined amount of time; and
determining that the accelerometer vector holds a steady absolute value equal or close to earth gravity acceleration for the predetermined amount of time.

3. The sports training aid of claim 1, wherein the processor is configured to determine the still position using a method including determining that gyro sensor's readings are confined within certain predefined limit values.

4. The sports training aid of claim 2, wherein the predetermined amount of time preferably is in the interval of 0.5 to 2.5 seconds, and even more preferred around 1.9 seconds.

5. The sports training aid of claim 2, wherein the determining of a steady absolute value includes checking that variation in accelerometer vector absolute value is within a predetermined interval preferably within +/− a percentage from earth gravity acceleration.

6. The sports training aid of claim 2, wherein the processor is configured to discard gyro sensor data when determining the still position.

7. The sports training aid of claim 1, wherein the user is an animal.

\* \* \* \* \*